United States Patent [19]

Miyazaki et al.

[11] Patent Number: 5,663,058
[45] Date of Patent: Sep. 2, 1997

[54] PROCESS FOR PRODUCING SOYBEAN PROTEIN MATERIAL

[75] Inventors: Tatsumi Miyazaki, Izumisano; Toru Kudo, Tsukuba-gun; Yasuo Otani, Izumisano; Motohiko Hirotsuka, Kaizuka, all of Japan

[73] Assignee: Fuji Oil Company, Limited, Osaka, Japan

[21] Appl. No.: 693,099

[22] PCT Filed: Dec. 7, 1995

[86] PCT No.: PCT/JP95/02504

§ 371 Date: Aug. 9, 1996

§ 102(e) Date: Aug. 9, 1996

[87] PCT Pub. No.: WO96/18311

PCT Pub. Date: Jun. 20, 1996

[30] Foreign Application Priority Data

Dec. 12, 1994  [JP]  Japan ..................... 6-306769

[51] Int. Cl.$^6$ .............. C07K 1/12; A23C 11/10; A23J 1/14; A23J 3/16
[52] U.S. Cl. ........................... 435/68.1; 530/378
[58] Field of Search ..................... 435/68.1; 530/378

[56] References Cited

U.S. PATENT DOCUMENTS 3,985,913  10/1976  Johnson et al. .............. 426/650
5,514,655  5/1996  DeWille et al. .............. 514/21

*Primary Examiner*—James Ketter
*Attorney, Agent, or Firm*—Wenderoth, Lind & Ponack

[57] ABSTRACT

There is disclosed a process for producing a soybean protein material which comprises the steps of: hydrolyzing soybean protein with a protease in an aqueous system to an extent of hydrolysis of 5 to 20; if necessary, emulsifying an oil-and-fat ingredient with soybean protein in an amount of 5 to 50 parts by weight per 100 parts by weight of the soybean protein before or after the hydrolysis step; drying the resultant emulsified mixture; and, optionally, a step for dispersing an emulsifier being provided at any stage after emulsification with the oil-and-fat ingredient. The soybean protein material thus obtained has taste, color and water-dispersibility suitable for a pickling solution having a high concentration and thick drinking food such as soup with less foaming property.

7 Claims, No Drawings

PROCESS FOR PRODUCING SOYBEAN PROTEIN MATERIAL

FIELD OF THE INVENTION

The present invention relates to a process for producing a soybean protein material, especially, a soybean protein powder having good water-dispersibility. It also relates to a process for producing a soybean protein powder having low solution viscosity and gel-forming ability upon heating. The soybean protein powder of the present invention is a soybean protein material suitable for using thick drinking food such as soup, pickling solutions and the like.

PRIOR ART

JP-B 48-24262 discloses a soybean protein product obtained by hydrolyzing soybean protein with a specific enzyme and spray-drying the hydrolyzed product and there is described that fats and oils, saccharides, vitamins and the like which have been pasteurized or sterilized separately can be added thereto before or after heat treatment. However, the product is a kind of oligopeptides having a low molecular weight such as that having a hydrolysis degree of about 24 of APL (average peptide length). Therefore, the product does not have gel-forming ability with sufficient water-solubility and whipping-ability and is unsuitable for thick drinking food and pickling solutions due to foaming.

In addition, JP-A 58-180796, a catalog of Lucas Meyer Corp. and the like teach methods for coating soybean protein with lecithin. However, they are not a method for dispersing soybean protein.

Further, JP-A 5-328939 discloses the use of a enzymatically hydrolyzed product of soybean protein as a pickling solution. JP-A 6-46799 discloses the use of a hydrolyzed product of soybean protein with an esterase as a pickling solution. However, any fats and oils are not used together with soybean protein and soybean protein is used alone.

On the other hand, when a past of a soybean protein powder (water-added and kneaded product) is heated, it forms a gel having good properties. Then, for example, a soybean protein powder is incorporated into a mixture of raw materials for meat products, or raw materials for meat products is soaked in a soybean protein solution. However, since a conventional soybean protein solution has high viscosity, there is such a problem that, when it is used as a solution for soaking, a large amount of a soybean protein solution cannot be incorporated into raw materials of meat products.

OBJECTS OF THE INVENTION

As indicated above, mere enzymatic hydrolysis of a soybean protein isolate causes lowering of gel-forming ability and increase in foaming and therefore, for preparation of thick drinking food such as soup or pickling solutions, there is a problem of workability. The main object of the present invention is to provide a soybean protein material having good flavor and color tone which has high salting-in property in so far as it has gel-forming ability satisfactory for a pickling solution, which is readily dispersed in water upon preparation of a pickling solution, which has less foaming ability so that a pickling solution having a high concentration can be prepared (i.e., with low viscosity), and which does not form a pool of a pickling solution after injection of the solution into ham.

SUMMARY OF THE INVENTION

In order to attain the above objects, the present inventors have studied intensively. As a result, it has been found that a soybean protein material, wherein the above problem in conventional soybean protein materials is improved, can be obtained by enzymatically hydrolyzing soybean protein to a certain extent, and by emulsifying the hydrolyzed soybean protein with a oil-and-fat ingredient in an aqueous system and, upon drying, dispersing an emulsifier in the resultant emulsified mixture and drying. Thus, the present invention has been completed.

That is, the first aspect of the present invention is a process for producing a soybean protein material which comprises the steps of hydrolyzing soybean protein with a protease in an aqueous system to a hydrolysis degree of 5 to 20; emulsifying an oil-and-fat ingredient with the soybean protein in an amount of 5 to 50 parts by weight per 100 parts by weight of the soybean protein before or after the hydrolysis step; and drying the resultant emulsified mixture. Optionally, after emulsification, a step for addition of an emulsifier to the soybean protein can be provided before or after the drying step.

The second aspect of the present invention is a process for producing a soybean protein material which comprises the steps of: hydrolyzing soybean protein with a protease in an aqueous system to a hydrolysis degree of 5 to 20; adding an emulsifier to the soybean protein and drying the resultant. The step for addition of the emulsifier can be conducted before or after the drying step.

In any of first and second aspects of the present invention, when the emulsifier is used, preferably, the emulsifier is present in an emulsified and dispersed state in an amount of 0.1 to 3 parts by weight per 100 parts by weight of solids content of the soybean protein.

The soybean protein material obtained by the process of the present invention is suitable for a pickling solution in addition to thick drinking food such as soup and the like.

DETAILED EXPLANATION OF THE INVENTION

The soybean protein to be used in the present invention is not specifically limited. However, as the soybean protein, suitably, there are soybean protein extracted from soybeans with water, soybean protein isolates, soybean protein concentrates and the like. Among them, normally, a soybean protein isolate is produced by extracting soybean protein from defatted soybeans with water and precipitating soybean protein at isoelectric point. A soybean concentrate contains an "okara (insoluble residue from soymilk production)" ingredient because it is not removed upon extraction with water.

The protease used in the present invention may be any proteases originated from vegetable (papain, buromelain, ficin, etc.), originated from animal (pepsin, trypsin, chymotoripsin, etc.), originated from microorganisms (Protin, Alkalase, Thermoase, etc). In addition, endo-proteases and a combination of endo- and exo-proteases and the like can be used. Any of acid proteases, neutral proteases, alkaline proteases and the like can be used. However, neutral proteases are preferred because neutralization is not required in the production steps.

A method for the enzymatic hydrolysis is not specifically limited and a hydrolysis temperature range and a pH range can be selected from the active temperature range and the active pH range of a particular protease to be used.

Although the amount of a protease varies according to the activity of a particular protease, normally, 0.05 to 5 parts by weight, practically 0.02 to 2 parts by weight of the protease is used per 100 parts of the soybean protein.

In addition, a hydrolysis degree of the soybean protein is adjusted to 5 to 20, preferably 6 to 15, wherein the hydrolysis degree is a ratio (%) of 0.22M trichloroacetic acid-soluble protein to the total proteins.

When the hydrolysis degree is less than 5%, increase in solution viscosity due to emulsification with the oil-and-fat ingredient as described hereinafter and denaturation of proteins due to decrease in moisture evaporation upon drying are liable to be caused. Thereby, salting-in property is liable to be lowered and viscosity becomes high, which results in difficulties in production of thick pickling solutions and thick drinking food such as soup. When the hydrolysis degree is more than 20, gel-forming ability is lowered and foaming is liable to cause in production of pickling solutions. This is not suitable.

Thus, according to the present invention, when the hydrolysis degree is in the range of 5 to 20, a pickling solution having a high concentration can be obtained by using the soybean protein material of the present invention because viscosity can be lowered without deterioration of salting-in property and sufficient gel-forming ability of the pickling solution can be provided. And yet, as described hereinafter, the pickling solution having less foaming property can be obtained by emulsifying the soybean protein with the oil-and-fat ingredient or dispersing an emulsifier therein, synergistically.

Furthermore, when the hydrolysis degree is maintained within such range, a peculiar flavor of soybean due to hydrolysis is not produced and, as described hereinafter, a pleasant flavor can be obtained by using the oil-and-fat ingredient together.

At the end of hydrolysis, heating can be carried out for inactivation of the enzyme as well as pasteurization or sterilization. Usually, heating at 80° to 160° C. for 3 seconds to 60 minutes is suitable. For industrial production, heating at 130° to 150° C. for 7 to 60 seconds can be carried out by using a high-temperature-short-time sterilizer or the like.

According to the present invention, problems of soybean proteins caused not only by enzymatic hydrolysis but also by using soybean proteins which violently foam and have a peculiar soybean flavor, dark color and the like can be solved by emulsifying the soybean protein with the oil-and-fat ingredient and/or an emulsifier.

As the oil-and-fat ingredient, according to particular use, there can be used vegetable fats and oils such as palm oil, coconut oil, soybean oil, cotton seed oil, corn oil, safflower oil, rice bran oil and the like, animal fats and oils such as beef fat, lard, fish oils, other animal fats and the like, fats and oils from microorganisms such as yeast, their fractionated, interesterified derivatives and the like. The operation for injecting a pickling solution into ham is carried out at a low temperature and, when the oil-and-fat ingredient to be used is solid or plastic at a low temperature (usually about 5° C.), increase in viscosity of a pickling solution or a pool of a pickling solution in the texture of ham may be caused. Therefore, the oil-and-fat ingredient to be used is preferably liquid at ordinary temperature. In particular, the oil-and-fat ingredient is preferably liquid at about 5° C. In thick drinking food such as soup and the like, semi-solid fats can be used.

The ratio of the enzymatic hydrolyzed soybean protein or soybean protein and the oil-and-fat ingredient is suitably 5 to 50 parts by weight, preferably 10 to 25 parts by weight of the oil-and-fat ingredient per 100 parts by weight of the enzymatic hydrolyzed soybean protein or soybean protein. When the amount of the oil-and-fat ingredient is too small, foaming upon preparation of a pickling solution is hardly inhibited. In addition, color of a tissue of ham injected with such a pickling solution tends to become dark and the peculiar soybean flavor also tends to be remained. On the other hand, when the amount of the oil-and-fat ingredient is too large, a white stripe pattern tends to form in a tissue of ham injected with such a pickling solution and it is undesirable. If the above ratio of the present invention is employed, the ham obtained has a bright colored tissue and pleasant taste, which results in high quality.

According to the present invention, the emulsion thus obtained or a dried material of the emulsion itself can be used as a raw material of thick drinking food such as soup and pickling solutions. However, preferably, an emulsifier is further dispersed therein. Even if an emulsifier is not used, a pickling solution having less foaming property, lower viscosity and more bright color in comparison with a conventional soybean protein can be obtained by the above enzymatic hydrolysis and emulsification with the oil-and-fat ingredient. However, when such an emulsifier is used together, water-dispersibility upon preparing a pickling solution can further be improved to increase workability and quality of ham injected with the pickling solution can be improved.

As the emulsifier used in the present invention, there can be used glycerin fatty acid esters, sucrose fatty acid esters, sorbitan fatty acid esters, propylene glycol fatty acid esters, polyglycerol fatty acid esters, polyglycerol condensed licynolate fatty acid ester, lecithins (inclusive enzymatic modified lecithins such as lysolecithin) and the like. They can be used alone or in combination thereof. Their hydrophilic or lipophilic nature is not specifically limited.

The emulsifier is suitably used in an amount of 0.1 to 3 parts by weight, preferably 0.2 to 2 parts by weight per 100 parts by weight of soybean protein solids in the emulsions. When the amount of the emulsifier is too small, only a litter effect on improvement of water-dispersibility upon preparation of a pickling solution and inhibition of foaming is expected. On the other hand, when the amount of the emulsifier is too much, an emulsifier flavor becomes strong and this is undesired. In case of thick drinking food such as soup, the situation is the same. In the present invention, the emulsifier is used not only for emulsification of the soybean protein, the oil-and-fat ingredient and water but also for other objectives such as inhibition of foaming and the like. In particular, preferably, the emulsifier is used in the already prepared emulsion mixture of the soybean protein and the oil-and-fat ingredient. That is, the emulsifier is dispersed in the emulsion mixture of the soybean protein and the oil-and-fat ingredient and then the resulting dispersion is dried to obtain an emulsified soybean protein powder, or the emulsifier is added after drying. When the emulsifier is emulsified with the already prepared emulsion mixture and is completely homogenized, only a little effect on inhibition of foaming is expected.

A method for drying is not specifically limited in so far as dried powder or granules can be obtained and, for example, spray drying, fluidized bed drying, freeze-drying or the like can be employed.

The following examples and comparative examples further illustrate the present invention in detail but are not to be construed to limit the scope thereof. In the following examples and comparative examples, all "percents" are by weight unless otherwise stated.

EXAMPLES 1–3 and COMPARATIVE EXAMPLES 1–4

Ten times volume of water was added to defatted soybeans and the mixture was stirred to extract soluble components. Then, the insoluble component, "okara", was removed to obtain soymilk. To this was added hydrochloric acid to adjust to pH 4.5. The precipitated protein was recovered and neutralized with sodium hydroxide to obtain a soybean protein isolate. This soybean protein isolate was warmed to 30° C. and a protease preparation (Amano Seiyaku K. K., "Protease B") was added thereto in an amount of 0.1% per solids content of the soybean protein. Enzymatic hydrolysis was carried out at 30° C. and pH 7.0 for 1 hour. Then, steam was blown into the reaction mixture and the enzyme was inactivated at 140° C. to obtain an enzymatic hydrolyzed soybean protein solution (hydrolysis degree: 10%).

To this enzymatic hydrolyzed soybean protein solution was added soybean refined oil in an amount of 10% based on the solids content of the soybean protein. The mixture was homogenized at pressure of 150 kg/cm² with a homogenizer to obtain an emulsified mixture. To the emulsified mixture was added and dispersed an emulsifier (sorbitan trioleate) in an amount of 0.5% based on the solids content of the soybean protein and the mixture was spray-dried to obtain the desired emulsified soybean protein material (Example 1).

At the same time, according to the same manner, the following soybean protein materials were obtained except that:

Example 2: no emulsifier was added;

Example 3: the emulsifier was added and the mixture was emulsified;

Comparative Example 1: no enzymatic hydrolysis was carried out;

Comparative Example 2: no enzymatic hydrolysis was carried out, no emulsifier was added and, after addition of soybean refined oil, the mixture was emulsified;

Comparative Example 3: only enzymatic hydrolysis was carried out and no soybean refined oil and emulsifier were added; and Comparative Example 4: no treatment was carried out, i.e. the soybean protein isolate itself.

Each soybean protein material thus obtained (8%), sodium caseinate (0.1%), corn powder (3.5%), whole milk powder (0.5%), skimmed milk powder (0.5%), seasoning (0.5%) and water (made up the total weight to 100%) were mixed and dissolved to prepare soup.

Water dispersibility upon admixing, foaming property, defoaming property and quality of the resultant soup were evaluated. The results are shown in Table 1.

TABLE 1

|  | Ex. No. | | | Comp. Ex. No. | | | |
| --- | --- | --- | --- | --- | --- | --- | --- |
|  | 1 | 2 | 3 | 1 | 2 | 3 | 4 |
| Enzymatic hydrolysis | Yes | Yes | Yes | — | — | Yes | — |
| Emulsification with oil-and-fat ingredient | Yes | Yes | Yes | Yes | Yes | — | — |
| Emulsifier | Disp. | — | Emul. | Disp. | — | — | — |
| Water-dispersibility | A | A | A | A | A | E | D |
| Foaming | A | B | B | B | C | E | D |
| Defoaming | A | C | B | C | D | D | E |
| Flavor of soup | A | A | A | A | A | B | B |
| Color of soup | A | A | A | A | A | B | B |
| Overall evaluation | A | C | B | C | D | E | E |

Yes: carried out, —: not carried out, Disp.: dispersed Emul.: emulsification

The hydrolysis degree is a ratio (%) of 0.22M trichloroacetic acid-soluble protein to the total proteins.

Water-dispersibility, flavor and overall evaluation were evaluated by the following criteria.

A: very good
B: somewhat good
C: average
D: somewhat bad
E: bad

Foaming was evaluated by the following criteria.

A: slightly foaming
B: somewhat foaming
C: considerably foaming
D: violently foaming
E: Only foam was observed.

Defoaming was evaluated by the following criteria.

A: very good defoaming
B: somewhat good defoaming
C: average
D: somewhat bad defoaming
E: considerably bad defoaming As seen from the results of Table 3, the most desired effect was obtained by conducting all of enzymatic hydrolysis, emulsification with the oil-and-fat ingredient and dispersion of the emulsifier. However, even when the emulsifier was emulsified, the resulting material could be served for a practical use, though foaming and defoaming were somewhat bad.

EXAMPLES 4 AND COMPARATIVE EXAMPLE 5

According to the same manner as described in Example 1, emulsified soybean protein materials were prepared by changing the amount of the protease, i.e., 0% (the same as Comparative Example 1), 0.03% (the same as Example 1), 0.25% and 0.50% (Comparative Example 5).

Each soybean protein material thus obtained (7%), egg white (5%), sodium caseinate (5%), salt (2.8%), sodium nitrite (0.02%), sodium L-ascorbate (0.06%), phosphate (0.7%), saccharides (5.0%), seasoning (0.3%), sodium succinate (0.02%), a coloring agent (0.2%) and water (made up the total weight to 100%) were mixed and dissolved to prepare a pickling solution.

The pickling solution (100 parts by weight) was injected into a raw material meat (a loin of Danish pork) from which a tendon and the like were removed (100 parts by weight) by an injector and subjected to tumbling at 5° C. for 10 to 20 hours with a rotary massage machine. The meat was filled in a casing and, after heating at 65° C. for 30 minutes, it was dried, smoked at 75° C. for 30 minutes, boiled at 78° C. for 120 minutes and cooled to obtain ham.

At this time, foaming and defoaming of the pickling solution and the tissue of the ham thus produced (pool of pickling solution, taste and texture) were evaluated. The results are shown in Table 2.

TABLE 2

|  | Comp. Ex. 1 | Ex. 4 No. 4 | Ex. 1 | Ex. 4 No. 5 | Comp. Ex. 5 |
| --- | --- | --- | --- | --- | --- |
| Protease | 0 | 0.03 | 0.1 | 0.25 | 0.5 |
| Hydrolysis degree | 4 | 6 | 10 | 20 | 30 |
| Viscosity | D | B | A | A | A |

TABLE 2-continued

|  | Comp. Ex. 1 | Ex. 4 No. 4 | Ex. 1 | Ex. 4 No. 5 | Comp. Ex. 5 |
| --- | --- | --- | --- | --- | --- |
| Foaming | B | A | A | B | C |
| Defoaming | C | A | A | A | B |
| Pool of pickling solution | C | B | A | A | A |
| Taste | A | A | A | A | C |
| Texture | A | A | A | B | D |
| Overall evaluation | C | B | A | B | C |

Foaming and defoaming were evaluated according to the same criteria as shown in Table 1.

Viscosity was evaluated according to the following criteria.

A: considerably low

B: somewhat low

C: average

D: somewhat high

E: considerably high

A pool of the pickling solution was evaluated according to the following criteria.

A: No pool of the pickling solution and no stripe was observed.

B: Only a little pool of the pickling solution and stripes were formed but almost indistinguishable.

C: Some pools of the pickling solution and stripes were formed but not noticeable.

D: Pools of the pickling solution and stripes were formed and somewhat noticeable.

E: Pools of the pickling solution and stripes were formed and considerably noticeable.

Texture was evaluated according to the following criteria.

A: Texture was uniform and feeling for chewing was good.

B: Texture was tender.

C: Texture was tender and somewhat brittle.

D: Texture was considerably tender and brittle.

E: Texture was considerably tender, brittle and dry.

As seen from the results of Table 2, the hydrolysis degree of 5 to 20 is suitable. When the hydrolysis degree was lower than this, viscosity becomes high and defoaming became difficult. On the other hand, when the hydrolysis degree was higher than the above, although viscosity was reduced, foaming upon preparation of the pickling solution was increased and the texture of ham was deteriorated.

EXAMPLES 5–6 AND COMPARATIVE EXAMPLE 6

According to the same manner as described in Example 1, emulsified soybean protein materials were prepared by changing the amount of soybean refined oil, i.e., 0% (Example 5), 5%, 10% (the same as Example 1), 25%, 50% and 100% (Comparative Example 6). According the same manner as described above, ham was produced by using each soybean protein material thus obtained.

At this time, states of the pickling solution and the tissue of the ham thus produced were evaluated. The results are shown in Table 3.

TABLE 3

|  | Ex. 5 Ex. 6 | Ex. 5 No. 6 | Ex. 1 | Ex. 5 No. 7 | Ex. 5 No. 8 | Comp. Ex. 6 |
| --- | --- | --- | --- | --- | --- | --- |
| Amount of oil-and-fat ingredient | 0 | 5 | 10 | 25 | 50 | 100 |
| Water-dispersibility | D | B | A | A | A | A |
| Foaming | C | B | A | A | A | A |
| Defoaming | B | A | A | A | A | A |
| Pool of pickling solution | D | C | A | A | C | D |
| Taste | C | B | A | A | A | A |
| Texture | B | A | A | A | B | D |
| Overall evaluation | D | B | A | A | B | D |

Evaluation was carried out according to the same criteria as shown in Tables 1 and 2.

As seen from the results of Table 3, although the oil-and-fat ingredient is not added, the texture of ham can be improved with less foaming, the amount of the oil-and-fat ingredient is suitably 5 to 50%. When the amount was smaller than this, water-dispersibility was deteriorated and a pool of the pickling solution was formed. When the amount was larger than the above, stripes were formed in the ham.

EXAMPLE 7

According to the same manner as described in Example 1, emulsified soybean protein materials were prepared except that soybean refined oil (15%) was added to the soybean protein isolate solution of Example 1, the mixture was emulsified and then enzymatically hydrolyzed with addition of the protease and the amount of the emulsifier was changed, i.e., 0.05%, 0.1%, 0.5% (the same as Example 1), 1.0%, 3.0% and 5.0%.

By using each material, soup was prepared according to the above 8% formulation and foaming was evaluated upon dissolution and quality of the resultant soup were evaluated. The results are shown in Table 4.

TABLE 4

|  | No. 9 | No. 10 | Ex. 1 | No. 11 | No. 12 | No. 13 |
| --- | --- | --- | --- | --- | --- | --- |
| Amount of emulsifier (%) | 0.05 | 0.10 | 0.50 | 1.0 | 3.0 | 5.0 |
| Foaming | B | B | A | A | A | A |
| Defoaming | C | A | A | A | A | A |
| Taste | A | A | A | B | C | D |
| Color | A | A | A | A | A | B |

As seen from the results of Table 4, the amount of the emulsifier is suitably 0.1 to 3.0%. When the amount was smaller than this, only a little effect on improvement of foaming and defoaming was expected. When the amount was larger than the above, the flavor of the emulsifier became strong and taste became bad. A smaller amount of the emulsifier is more desirable from the view point of the flavor and, when emulsification was carried out as Example 3, its improvement effect was reduced and, for obtaining the same effect, a larger amount of the emulsifier was required.

As described hereinabove, the emulsified soybean protein material of the present invention is readily dispersed and dissolved upon production of a pickling solution. And foaming is inhibited upon production and application to ham. In addition, viscosity is low and therefore it is possible to produce a pickling solution having a high concentration and to inject a large amount of the pickling solution. Further, is it has an excellent gel-forming ability and therefore it is suitable for a soaking solution of ham. Furthermore, the ham produced by using the pickling solution has good meat taste without soybean flavor, bright color and high commercial value and has good quality without a pool of the pickling solution and stripe. When the material of the present invention is utilized as a protein source of drinking food and the like, it shows good dispersion and dissolution as well as good workability because of less foaming. Further, when it is used for soup, drinking and the like, it shows good dispersion with inhibiting foaming and good taste.

What is claimed is:

1. A process for producing a soybean protein material which comprises the steps of: hydrolyzing soybean protein with a protease in an aqueous system to a hydrolysis degree of 5 to 20; emulsifying an oil-and-fat ingredient with soybean protein in an amount of 5 to 50 parts by weight per 100 parts by weight of the soybean protein before or after the hydrolysis step; and drying the resultant emulsified mixture.

2. A process according to claim 1 which further comprises a step for addition of an emulsifier.

3. A process according to claim 1, wherein 0.1 to 3 parts by weight of the emulsifier is added per 100 parts by weight of solids of the soybean protein.

4. A process according to claim 1, wherein the soybean protein material is to be used for a pickling solution.

5. A process for producing a soybean protein material which comprises the steps of: hydrolyzing soybean protein with a protease in an aqueous system to a hydrolysis degree of 5 to 20; adding an emulsifier and then drying the resulting mixture.

6. A process according to claim 5, wherein 0.1 to 3 parts by weight of the emulsifier is added per 100 parts by weight of solids of the soybean protein.

7. A process according to claim 1, wherein the soybean protein material is to be used for a pickling solution.

* * * * *